United States Patent [19]

Bloom

[11] 4,338,924

[45] Jul. 13, 1982

[54] CARDIOPULMONARY RESUSCITATION DEVICE

[76] Inventor: Charles S. Bloom, 1400 NW. 10 Ave., 19E, Miami, Fla. 33136

[21] Appl. No.: 208,544

[22] Filed: Nov. 20, 1980

[51] Int. Cl.³ ............................................ A61H 31/00
[52] U.S. Cl. ................................. 128/28; 128/205.25
[58] Field of Search ................... 128/205.24, 205.25, 128/205.18, 205.16, 28

[56] References Cited

U.S. PATENT DOCUMENTS

| | | | |
|---|---|---|---|
| 2,484,306 | 10/1949 | McClain et al. | 128/28 |
| 3,209,747 | 10/1965 | Guentner | 128/28 |
| 3,209,748 | 10/1965 | Thomas | 128/28 |
| 3,219,031 | 11/1965 | Rentsch, Jr. | 128/28 |
| 3,254,645 | 6/1966 | Rand et al. | 128/28 |
| 3,425,409 | 2/1969 | Isaacson et al. | 128/28 |
| 3,965,893 | 6/1976 | Ragailler | 128/28 |

*Primary Examiner*—Richard C. Pinkham
*Assistant Examiner*—T. Brown
*Attorney, Agent, or Firm*—John Cyril Malloy

[57] ABSTRACT

A device is disclosed for administering cardiopulmonary resuscitation to a heart attack victim. The device includes a frame comprised of a main support base assembly and an upright portion with a top arm portion which is pivoted intermediate its length to the upright. A conventional air cylinder assembly is pivotally connected between first ends of the base assembly and pivotal arm to actuate the pivotal arm to apply appropriate pressure to the chest area of a victim, disposed in a prone position beneath an abutment member, adjustably carried by a second end of the pivotal arm. A conventional tank of pressurized oxygen is connected to a pneumatic system to cyclically operate the air cylinder assembly to apply the pressure to the chest area and to feed the oxygen through a conventional face mask, connected in the pneumatic system and disposed over the nose and mouth area of the victim. The upright portion is collapsible on the base assembly for storage purposes.

22 Claims, 7 Drawing Figures

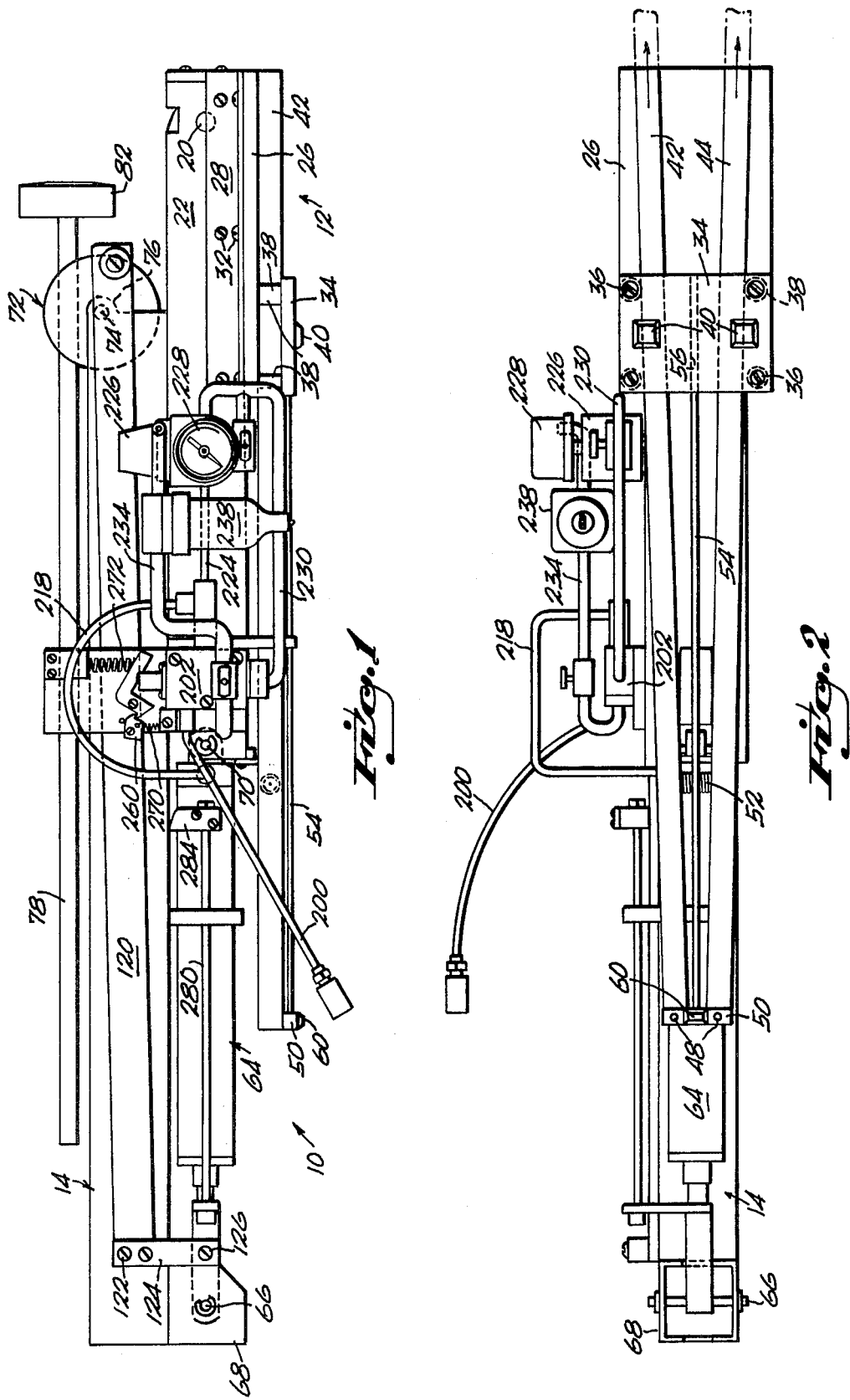

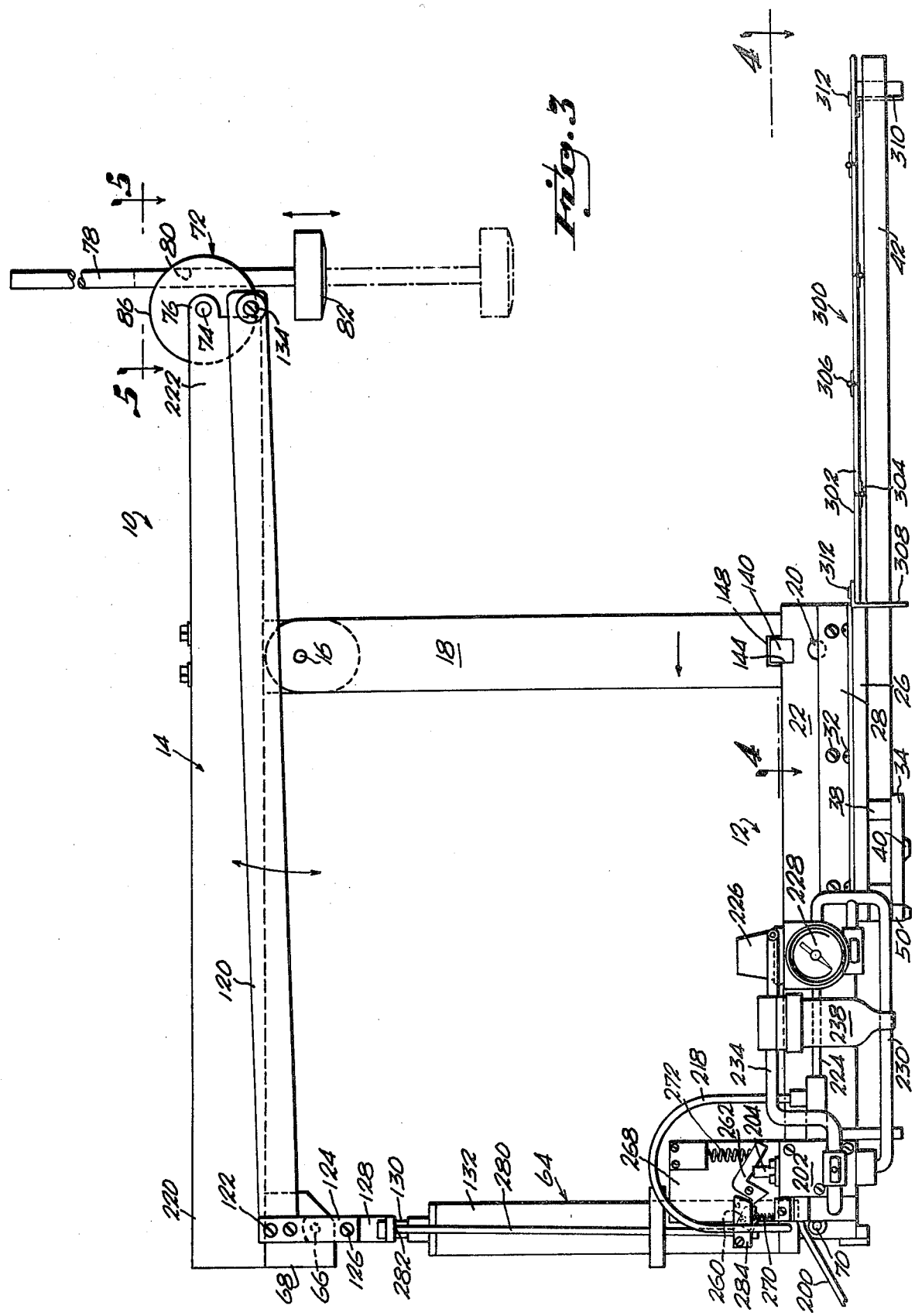

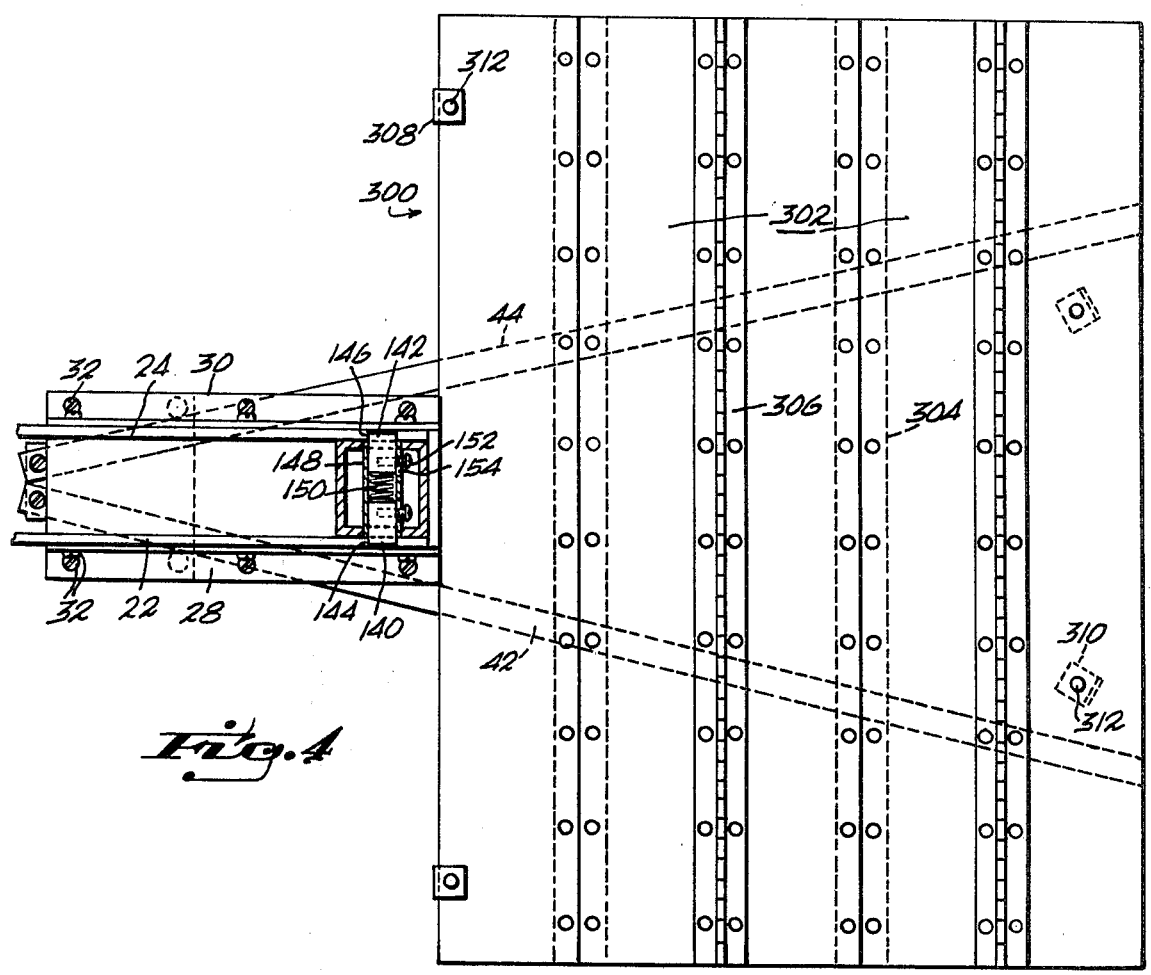
Fig.4
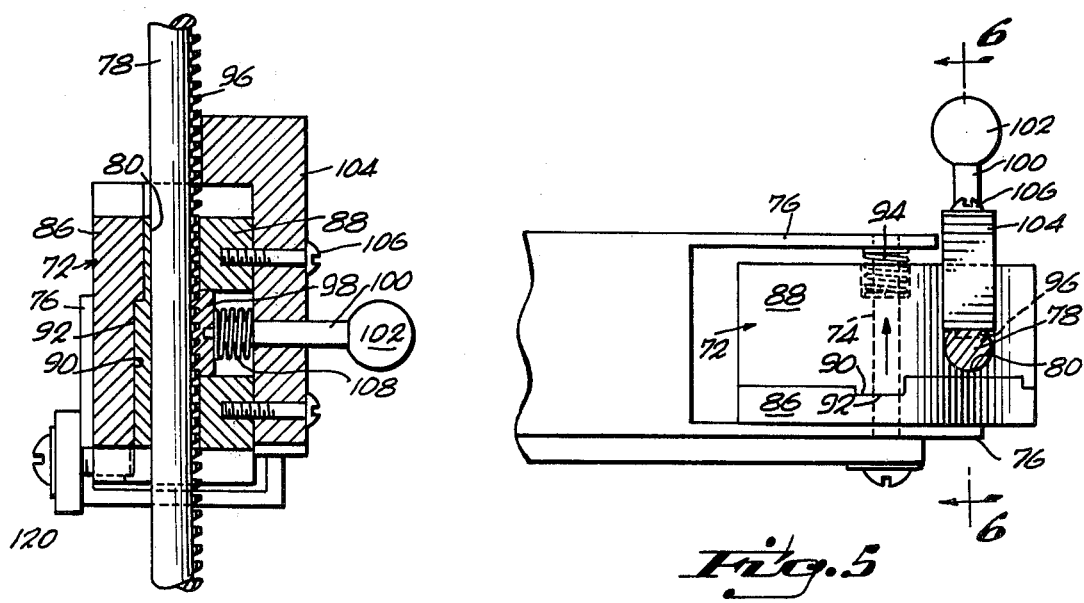
Fig.6
Fig.5

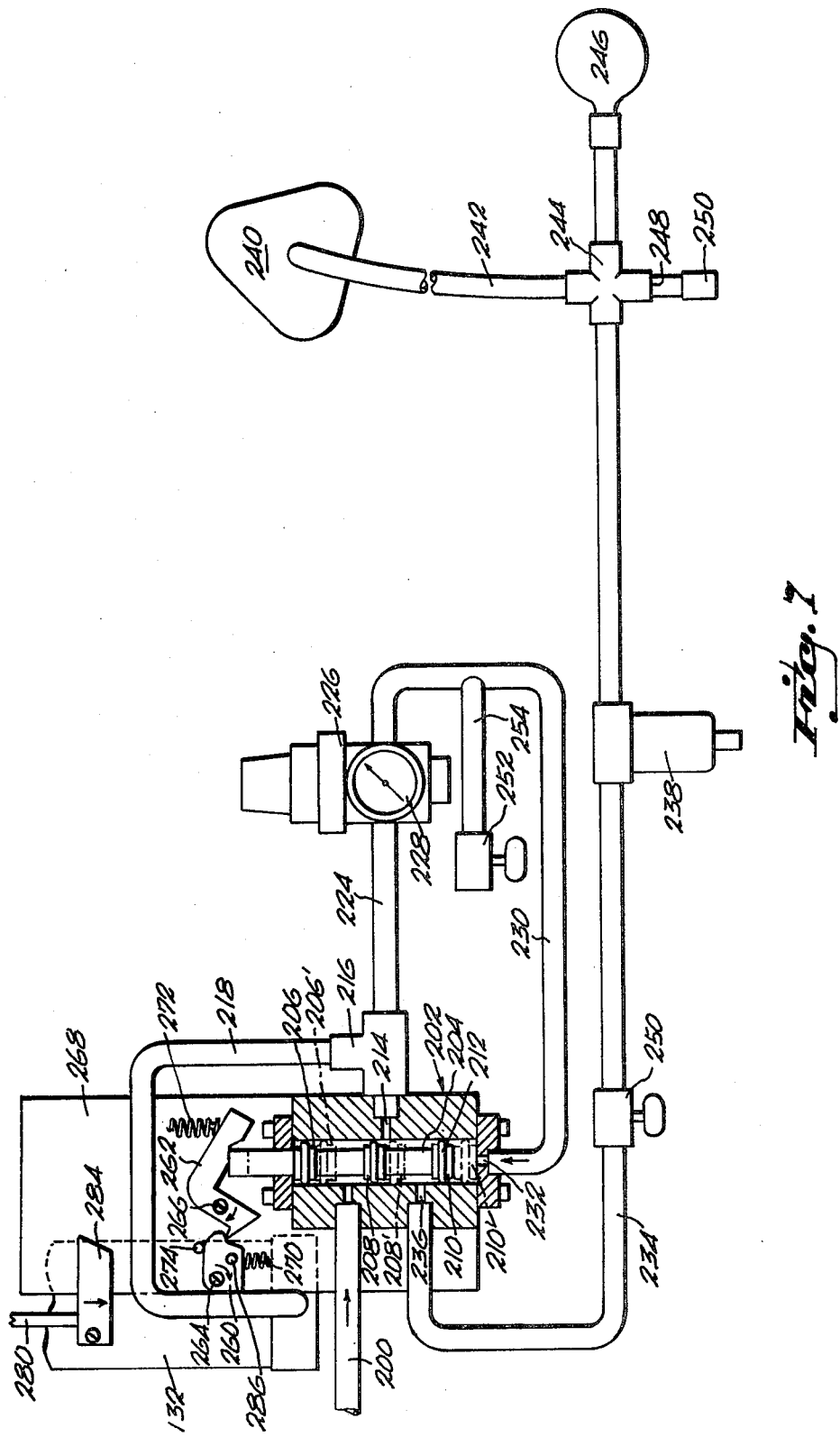

CARDIOPULMONARY RESUSCITATION DEVICE

BACKGROUND OF THE INVENTION

As is well known, it is imperative that a heart attack victim receive immediate aid in the form of cardiopulmonary resuscitation after suffering the attack. However, a great majority of the general public are unaware of, or inept in the necessary procedures to administer the necessary help to the victim, and the time lost in calling and waiting for competent professional help, is often fatal to the victim.

Therefore, one of the principal objects of the present invention is to provide a device which is readily operable to administer cardiopulmonary resuscitation to a heart attack victim.

A further object of the invention is to provide a device of this nature which is very easy to use, and which utilizes a commercially available pressurized container of oxygen to accomplish both the pumping action on the heart area of the chest and the administration of oxygen, under pressure, into the lungs of the victim through the nose and mouth.

Yet another object of the invention is to provide a device which is very simple in operation, is compact in size and is collapsible for easy storage in a relatively small area in a home, office, factory, automobile, etc.

BRIEF DESCRIPTION OF THE DRAWINGS

FIG. 1 is a side elevational view of the cardiopulmonary resuscitation device of the present invention in a collapsed condition;

FIG. 2 is a bottom plan view of FIG. 1;

FIG. 3 is a side elevational view of the device of FIG. 1, in an erected condition;

FIG. 4 is a fragmentary sectional view taken along line 4—4 of FIG. 3;

FIG. 5 is a fragmentary sectional view taken along line 5—5 of FIG. 3;

FIG. 6 is a fragmentary sectional view taken along line 6—6 of FIG. 5; and

FIG. 7 is a semi-schematic illustration of the pneumatic operating structure of the device.

DETAILED DESCRIPTION OF THE DRAWINGS

With reference to the drawings, and particularly to FIGS. 1 and 3, which respectively illustrate the device, indicated generally at 10, in a collapsed and erected condition, and which includes a main base assembly 12 and a collapsible upper beam 14 pivotally connected, intermediate its length, at 16 to a post 18 which is pivotally connected at 20 between a pair of upstanding side walls 22, 24 of the base assembly 12, FIGS. 1 3 and 4.

The side walls 22, 24 are secured to a bottom plate 26 by opposed angle members 28, 30 and screws 32. An inverted bridge plate 34, FIGS. 1, 2 and 3, is fixed by four corner screws 36 to the underside of bottom plate 26, plate 34 being spaced from the underside by respective spools 38 surrounding screws 36 between plates 26 and 34, and a pair of support pads 40 are secured in a laterally spaced relation to the bottom of plate 34.

With particular reference to FIGS. 1, 2, 3 and 4, a pair of extendible legs 42, 44 are slidably engaged between plates 26 and 34 in a confined relation between the spools 38. At their rear ends, extendible legs 42, 44 are pivotally attached at 48 to respective ends of a cross bar 50 and a compression spring 52 is confined between legs 42, 44 to maintain an outwardly directed pressure therebetween. A center guide rod 54 is secured at a rear end in cross bar 50 and extends forward through a hole 56 in plate 34. Therefore, the legs 42, 44 in a retracted position in FIG. 2, may be slid forwardly to the extended position of FIGS. 3 and 4, with an increased degree of divergence, until the cross bar 50 contacts the plate 34. A support pad 60 is secured to the bottom side of cross bar 50.

A conventional spring-loaded air cylinder and piston assembly 64 is pivotally attached at 66, at an upper end, to a downward rear end extension 68 of the upper beam 14, and is pivotally attached at 70 between rear ends of the side walls 22, 24.

A disc assembly 72 is rotatably carried on a pin 74, secured between front ears 76 of the beam 14, and an elongated rod 78 extends through a chordally disposed hole 80 in disc assembly 72 and carries a chest abutment member 82 in a fixed relation to a lower end thereof. With particular reference to FIGS. 5 and 6, the disc assembly 72 includes two disc portions 86, 88 with mating offset abutting face portions at 90, 92 which normally keys portions 86, 88 together. However, with reference to FIG. 5, the disc portion 88 is spring-loaded at 94 to normally maintain the keyed relationship therebetween while permitting manual axial and rotational movement of disc portion 88 to rotate the rod 78 and chest abutment member 82 to the retracted position of FIG. 1.

As further illustrated in FIGS. 5 and 6, one side of the rod 78 includes a line of teeth 96 along a major length thereof for selective engagement by a toothed segment 98, secured to an outwardly extending rod 100, provided with a handle knob 102, exteriorly of a bracket 104 secured by screws 106 to disc portion 88. The segment 98 is spring-loaded at 108 against bracket 104 whereby the rod 78 and chest abutment member 82 may be vertically adjusted to accommodate individual heart attack victims therebeneath.

With particular reference to FIGS. 1 and 3, an elongated link 102 fixed at 122 to a lever 124 which, in turn, is fixed at 126 to an extension 128 of the piston rod 130 of the cylinder 132 of the cylinder and piston assembly 64. Elongated link 120 is secured by a screw 134, at a second end, to the disc portion 88 and serves to automatically pivot the rod 78 and chest abutment means from the vertical position, FIG. 3, to the horizontal position, FIG. 1, when the device is operated to a collapsed condition.

Referring to FIGS. 3 and 4, a pair of latch buttons 140, 142, extend through notches 144, 146 in respective side walls 22, 24 to normally maintain the device in the erected position of FIG. 3. When buttons 140, 142 are simultaneously depressed into the tube 148, against the forces of a compression spring 150, the device 10 may be pivotally collapsed about pivot pins 20 and 70 to the condition of FIGS. 1 and 2. A keeper screw 152 extends through a slot 154 in tube 148 from each button 140, 142.

The operation of the device from a pressurized oxygen source will be related generally to FIG. 7, with references to FIG. 3. The pressurized oxygen source may be a conventional commercially available oxygen container (not shown) connected to a conduit 200, opening into a valve 202 having a two position spool 204 provided with three lands 206, 208 and 210, each provided with a seal ring 212. In a first position as in FIG. 1, the lands will be in the dot-dash phantom positions of FIG. 7 indicated at 206', 208', and 210'. In this phantom position, the pressurized oxygen from conduit 200 will pass from conduit 200 into port 214, through T 216 and conduit 218 to the bottom of cylinder 132, driving the piston and piston rod assembly 130 upwardly to raise the rear end 220 of beam 14, driving the forward end 222 and the rod and chest abutment 78, 82 downwardly about pivot 16.

When the piston and rod assembly 130 reaches its upper limit, the oxygen pressure in conduit 224, connecting from T 216 to a pressure regulator 226 having a gauge 228, increases, overides the pressure setting of regulator 226, and passes through the pressure regulator 226, conduit 230 and a bottom port 232 to shift the spool 204 upwardly to position the lands in the full line positions 206, 208 and 210. Pressure in the cylinder 132 is relieved and the conventional built-in spring-loading thereof returns the piston and rod assembly 130 downwardly forcing the oxygen in the cylinder 132 outwardly through conduit 218, port 214 and into conduit 234 by way of port 236.

The oxygen flows through conduit 234, and a conventional filter device 238 to a conventional face mask 240 by way of a flexible conduit 242. If desired, a four-way fitting 244 may be connected to conduit 234 with a balloon 246 attached thereto to sequentially inflate and deflate to indicate proper operation of the device, and to provide an opening at 248 for connection to a peep valve 250, opening to the atmosphere to vent off a controlled portion of the oxygen. A shut-off valve 250, may be interposed in conduit 234 and a similar shut-off valve 252 may be connected to a conduit 254 from conduit 230 for venting purposes.

With further reference to FIG. 7, and FIG. 3, a pair of cooperating latch members 260, 262 are pivotally fixed at 264, 266 to a mounting plate 268, fixed to side wall 22. Latch members 260, 262 are spring-loaded at 270, 272 to maintain the latched condition of FIG. 7 by means of a stop pin 274 fixed in plate 268. As illustrated in FIG. 3, a rod 280 is fixed at an upper end at 282 to the outer end of the piston and piston rod assembly 130, and a latch trip finger 284 is carried in a fixed relation to the lower end of rod 280 in a position to contact a trip pin 286, extending outwardly from latch member 260, at the bottom of the stroke of the piston and piston rod assembly 130 to disengage the latch members 260, 262. Compression spring 272 of latch member 262, which bears against the top end of valve spool 204, thereby returns the valve spool 204 to the lower phantom position 206', 208', and 210'. The latches 260 and 262 are engaged at the top of each stroke of piston and piston rod assembly, by contact by the valve spool 204, when the oxygen pressure is diverted through conduit 224 and pressure regulator 226, and are disengaged at the bottom of each stroke as above described.

Therefore, the continuous up-down cycles are imparted to the rod 28 and chest abutment member 82, in response to the flow of pressurized oxygen, when the device is in operation.

A back support platform 300, which lies across the legs 42, 44 in their extended positions, is provided for the heart attack patient who is placed thereon, in a prone position, with his chest area positioned relative to the chest abutment member 82 which is properly adjusted, as to height, relative to the patient's chest.

In a preferred form, the back support platform 300 is comprised of a plurlity of plate members 302 which are alternately hinged together on opposite sides as at 304, 306 whereby the plates may be folded into a stacked relation for storage purposes. Pairs of downwardly extending inner and outer feet 308, 310 are secured at 312 to the opposed end plates 302 for stability purposes.

When the device is operated as above described and the chest abutment member is properly positioned, a pressure is exerted on the patient's chest and oxygen is provided to the nose and mouth area of the patient in a continuous sequential order.

As used in this specification, the term "peep valve" is of a valve known in the trade as a "positive end expiratory pressure." It is a pressure relief valve which maintains a pressure in the line at all times and allows pressure to build up to a predetermined level and, thereafter, any pressure over and above that is allowed to escape. A typical peep valve is in the shape of a plastic cone wherein the larger end is the inlet and the smaller end is the outlet and, in the side wall of the cone adjacent the smaller end, a slit is provided which is normally closed but, in response to an undesired high pressure within the cone, opens slightly so that the pressure escapes through the slit which is opened by the internal pressure. In FIG. 1, when the latch member 260 is in the position shown, the spring 272 is compressed; however, for illustrative purposes the same is shown in this view as illustrated, it being pointed out that in FIG. 3 the spring 272 is as shown in relation to the latch member 62.

While a preferred form of the present invention has been herein described, it will be evident to those skilled in the art that various changes and modifications can be made therein without departing from the true spirit of the invention as defined in the appended claims.

What is claimed is:

1. A device for administering cardiopulmonary resuscitation to a heart attack victim comprising, a main horizontally disposed base, a normally upstanding post from said base, pivotally attached at an upper end intermediate the length of a generally horizontally extending upper beam member, a spring-loaded pneumatic cylinder and piston assembly, pivotally connected between respective rear end portions of said base and beam, a chest abutment member adjustably suspended in a generally vertical attitude relative to a front end of said beam, and valve means connected in a pneumatic system to receive a flow of pressurized oxygen from a suitable source such as a commercially available presurized oxygen tank, and means to continuously sequentially operate said valve means to, first, direct a flow of pressurized oxygen through said system to said cylinder to actuate said piston in a manner so as to rock said beam about said intermediate upper end pivot to cause said chest abutment to descend into contact with and to exert a pressure on the heart area of a heart attack victim positioned therebeneath, and, second, to exhaust said oxygen in said cylinder through said system under the influence of said spring-loading, and to direct said exhausted oxygen through said valve means and a conduit connecting to a face mask for positioning over the nose and mouth area of the victim.

2. The device as defined in claim 1 wherein said valve means is a two position spool type valve which, in a first position, directs the flow of pressurized oxygen from said source to a bottom portion of said cylinder to extend said piston vertically to rock said beam and, in a second position, directs said oxygen from said cylinder bottom portion to said face mask, permitting said piston and chest abutment means to retract.

3. The device as defined in claim 2 wherein said means to sequentially operate includes a pressure regulator, in said pneumatic system, in a position to direct the pressurized oxygen from said tank to a bottom end of said spool valve to shift same to said second position after said piston is fully extended, thereby opening said cylinder bottom end through said valve to said face mask.

4. The device as defined in claim 3 wherein said means to sequentially operate also includes a latch means comprised of a pair of adjacent coacting pivotal latch members which are located relative to said valve means, and are spring-loaded in a manner whereby they are latched relative to each other by an outwardly extended end of said spool valve with said spool valve in said second position.

5. The device as defined in claim 4 wherein said means to sequentially operate further includes a trip means, carried by said cylinder piston, and extending downwardly into a position to contact an outward projection from a first of said latch members to trip same to an unlatched condition when said piston is fully retracted, thereby permitting spring-loading of a second of said latch members, contacting said spool valve extended end to shift said spool valve back to said first position for the start of a next cycle under the influence of the pressurized oxygen.

6. The device as defined in claim 1 including a balloon connected to said face mask conduit to visibly indicate proper operation of the device.

7. The device as defined in claim 1 wherein said chest abutment member is a generally disc-shaped member carried in a lower end of an elongated rod.

8. The device as defined in claim 7 wherein said adjustable suspension includes a disc-shaped assembly, pivotally journalled between front end side wall extensions of said beam member with a chordally disposed hole formed therein for sliding reception of said elongated rod.

9. The device as defined in claim 8 wherein said adjustable suspension also includes a plurality of aligned teeth defined along a major length of one side of said elongated rod and spring-loaded detent means engaged through a bracket fixed to one side of said disc assembly for selective engagement along the length of said teeth.

10. The device as defined in claim 9 including a toothed segment, fixed to an inner end of said detent means for selective engagement with said aligned teeth.

11. The device as defined in claim 9 wherein said disc-shaped assembly includes a major disc-shape portion carrying said elongated rod, and a minor disc-shaped portion, said major and minor portions including mating offsets defined in confronting faces thereof defining a keyed relationship therebetween when said faces are disposed in a contacting relation to each other, and including a compression spring disposed about said pivotal journal between said major disc portion and one of said side wall extensions, with a space between said one side wall and major disc portion which is sufficient to permit said major disc portion to be retracted and rotated relative to the other of said disc portions.

12. The device as defined in claim 11 including elongated link means pivotally connected between said minor disc-shaped portion and an upper extension of said piston.

13. The device as defined in claim 1 wherein said upstanding post is pivotally attached at a bottom end portion between a pair of upstanding side walls of said base, and including transverse spring-loaded latch means slidably engaged in said post bottom end, above said pivotal attachment, for normal latched engagement with said side walls to maintain said post and cylinder and piston assembly in generally upright positions with said horizontal beam spanning upper ends thereof, said spring-loaded latch means being depressible to an unlatched condition relative to said side walls to permit said post, cylinder and piston assembly, chest abutment member and horizontal beam to be collapsed on top of said base.

14. The device as defined in claim 1 including a pair of pivotally connected slidable legs, normally disposed in a retracted position beneath said base and being slidably extendible to positions extending beyond said chest abutment member, and including an inverted bridge means, fixed to a bottom wall of said base, and spanning said legs, to confine said legs to sliding movement between said retracted and extended positions.

15. The device as defined in claim 14 including a cross bar, pivotally connected between rear ends of said legs, for contact with a rear end of said bridge means at a fully extended position of said legs.

16. The device as defined in claim 15 wherein said rear end cross bar is substantially narrower than the span of said bridge permitting a substantial increase in an outwardly diverging angular relation between the pair of legs as they are slid from said retracted to extended positions beneath said chest abutment means.

17. The device as defined in claim 16 including a back support member, for the victim, disposed on top of said leg extensions.

18. The device as defined in claim 17 wherein said back support member is comprised of a plurality of longitudinally extending plates, alternately hinged together on opposite sides to permit the folding of the plates into a stacked condition when not in use.

19. The device as defined in claim 18 including a plurality of legs fixed to said opposed side edges of said back support, said legs spanning a vertical thickness of said legs to engage against a support surface such as a floor.

20. The device as defined in claim 1 including an inflatable balloon connected in communication with said face mask conduit.

21. The device as defined in claim 20 including a peep valve connected in communication with said face mask conduit.

22. The device as defined in claim 1 including a filter means connected in said face mask conduit.

* * * * *